US006973434B2

(12) United States Patent
Miller

(10) Patent No.: US 6,973,434 B2
(45) Date of Patent: Dec. 6, 2005

(54) COMPUTER-BASED SYSTEM FOR AUTOMATING ADMINISTRATIVE PROCEDURES IN AN OFFICE

(75) Inventor: Geoffrey Marc Miller, Manhattan Beach, CA (US)

(73) Assignee: MillerMed Software, Inc., Manhattan Beach, CA (US)

( * ) Notice: Subject to any disclaimer, the term of this patent is extended or adjusted under 35 U.S.C. 154(b) by 0 days.

(21) Appl. No.: 09/227,406

(22) Filed: Jan. 8, 1999

(65) Prior Publication Data

US 2003/0097277 A1 May 22, 2003

Related U.S. Application Data

(60) Provisional application No. 60/070,884, filed on Jan. 9, 1998.

(51) Int. Cl.[7] ............................................. G06F 17/60
(52) U.S. Cl. ................................. 705/2; 705/3; 705/8
(58) Field of Search .............................. 705/2, 3, 7, 8, 705/9

(56) References Cited

U.S. PATENT DOCUMENTS

| 5,065,315 A | | 11/1991 | Garcia ................... 364/413.01 |
| 5,146,439 A | * | 9/1992 | Jachmann et al. ............. 369/25 |
| 5,319,543 A | | 6/1994 | Wilhelm ..................... 364/401 |
| 5,359,509 A | | 10/1994 | Little et al. ................. 364/401 |
| 5,557,514 A | | 9/1996 | Seare et al. ................. 364/401 |
| 5,772,585 A | * | 6/1998 | Lavin et al. ................. 600/300 |
| 5,822,544 A | * | 10/1998 | Chaco et al. ............... 395/202 |
| 5,823,948 A | * | 10/1998 | Ross, Jr. et al. ............ 600/300 |
| 5,875,436 A | * | 2/1999 | Kikinis ........................ 705/34 |
| 5,924,074 A | * | 7/1999 | Evans ........................... 705/3 |
| 5,946,659 A | * | 8/1999 | Lancelot ....................... 705/3 |
| 5,974,389 A | | 10/1999 | Clark et al. .................... 705/3 |
| 5,995,937 A | * | 11/1999 | DeBusk et al. ................ 705/2 |

FOREIGN PATENT DOCUMENTS

WO    WO009628086 A1 * 9/1996

OTHER PUBLICATIONS

Steven M. Ornstein et al., "A Vendor Survey of Computerized Patient Record Systems", Family Practice Management, Feb. 1996.*
"Computer-based Patient Record System Description of Functionality", Computer-based Patient Record Institute, Aug. 1996.*
Steven M. Ornstein et al., "Computerized Patient Record Systems: A Survey of 28 Vendors", Family Practice Management, Nov./Dec. 1997.*
Ellen Messmer, "MedicaLogic readies distributed patient information software", Network World, Jun. 5, 1995, p. 37.*
MedicaLogic Press Releases: Jan. 27, 1997, Feb. 17, 1997, Oct. 27, 1997, and Nov. 10, 1997.*
Lynne Dunbrack, "Practice-management market to reach $1 billion by 1999", Health Management Technology, Jun. 1996, p. 31-34.*
Mary K. Kerrigan, "A New Profit Center", Computers in Healthcare, Dec. 1987, p. 33-36.*
Lenny Liebmann, "Feeling Right at Home," LAN Magazine, Jun., 1996, at 121.
"Savings for Physical Therapists," Electronic Messaging News, Apr. 17, 1996.

* cited by examiner

Primary Examiner—Hani M. Kazimi
(74) Attorney, Agent, or Firm—Kenyon & Kenyon

(57) ABSTRACT

A computer-based system for automating administrative procedures in a medical office is described. The system includes a control module in communication with an administrator module and a tape management module, as well as a database accessible by the administrator module and the tape management module. The tape management module can advantageously be configured, for example, to manage outsourcing of tape transcription.

24 Claims, 6 Drawing Sheets

COMPUTER-BASED SYSTEM FOR AUTOMATING ADMINISTRATIVE PROCEDURES IN AN OFFICE

This application claims the benefit under 35 U.S.C. § 119(e) of U.S. Provisional Application No. 60/070,884, filed Jan. 9, 1998.

BACKGROUND OF THE INVENTION

The present invention is directed generally to the field of office automation, and in particular to a computer-based system for automating administrative procedures in a medical office. In accordance with particular embodiments of the invention disclosed herein, various administrative procedures that would otherwise require substantial manpower to complete are instead performed by an integrated computer system that performs those administrative procedures in an efficient, cost-effective manner. As a result, substantially less manpower is required to run a medical office, thereby reducing overhead costs.

It is well-recognized that the single largest expense in a medical office is personnel, and that the processing of documents generates the majority of the labor in a medical office. As service providers, however, physicians and medical office staff should ideally be spending their time on patient care, and not on document management. Time lost to administrative duties is all the more critical in view of the trend towards managed health care, leading to reduced medical fees but increased overhead costs.

There are literally hundreds of medical software applications available today. The majority of these applications deal with billing, scheduling, medical records, and most recently, outcome management. In addition, there are report generators, online services, and efforts to move towards a so-called "paperless office." While such tools can be helpful, none of them directly address the most costly component of medical office overhead—labor hours.

There is therefore a need to reduce the manpower required to complete office administration tasks typically required in a medical office, such as tape transcription, chart preparation, report generation, and forms generation. Embodiments of the present invention meet that need.

SUMMARY OF THE INVENTION

The present invention is directed to a computer-based system for automating administrative procedures in a medical office. In accordance with a first embodiment of the present invention, such a system includes a control module in communication with an administrator module and a tape management module, as well as a database accessible by the administrator module and the tape management module. The tape management module can advantageously be configured, for example, to manage outsourcing of tape transcription. In a variation on this embodiment, a provider module is configured, for example, to generate reports directed to the needs of service providers (e.g., daily task lists, workload reports, chart locations, tape transcription status, record review status, etc.) as opposed to administrative staff, thus enabling the system to be geared towards the providers themselves in a way not typically found in existing medical office software.

In accordance with another embodiment of the present invention, a computer implemented method for automating administrative procedures in a medical office is provided. Such a method includes the steps of maintaining a database including provider information, patient information, and document management information; using the database to automatically generate management reports identifying tasks to be performed on a given day; automatically generating reports associated with the tasks to be performed, populating the reports with information from the database as appropriate; and supporting off-site performance of one or more administrative tasks, including managing electronic information exchanges with off-site service providers.

In accordance with another embodiment, a computer-implemented subscription service for automating administrative procedures in a medical office is provided. In providing such a subscription service, one or more medical offices are provided with an office automation system including a communications interface for receiving data electronically. A service center receives a request for office administration services from such a medical office, processes the request, and electronically transmits information relating to the processed request to the office automation system at the requesting medical office. Services that can be provided in this manner include, for example, tape transcription, chart preparation, record review, report generation, and forms generation.

These and other embodiments are described in detail below. Persons in the field of medical services will appreciate that embodiments of the present invention enable providers of medical services to streamline administrative operations in a way not possible with prior medical software applications, allowing for significant reductions in overhead attributable to administrative staffing requirements.

DETAILED DESCRIPTION

The present invention is directed generally to computer-based systems for automating administrative procedures in a medical office. In accordance with particular embodiments of the invention, various administrative procedures that would otherwise require substantial manpower to complete are instead performed by an integrated computer system that performs those administrative procedures in an efficient, cost-effective manner. As a result, substantially less manpower is required to run a medical office, thereby reducing overhead costs. In addition, systems configured in accordance with the present invention enable providers and/or office administrators to become more independent from support staff than is possible in a typical medical office.

Figure 1:
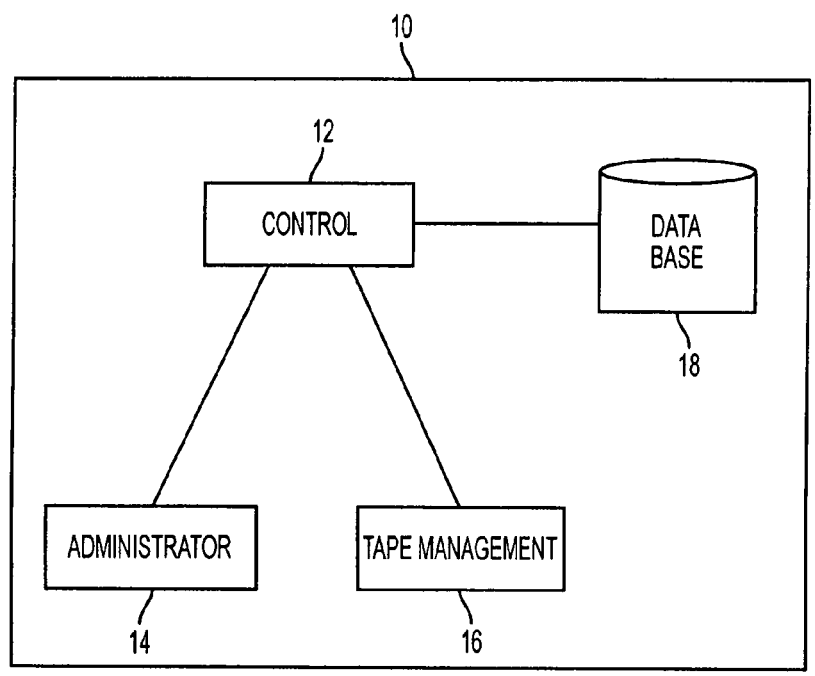
FIG. 1 is a block diagram illustrating a computer-based system for automating administrative procedures in a medical office in accordance with an embodiment of the present invention.

Referring now to FIG. 1, in accordance with a first embodiment of the present invention, a office automation system 10 for automating administrative procedures in a medical office includes a control module 12 in communication with an administrator module 14 and a tape management module 16. In addition, office automation system 10 has access to a database 18. In the illustrated embodiment, control module 12, administrator module 14 and tape management module 16 comprise software modules coded in, for example, the C++ programming language. Alternatively, suitable code can be readily generated using a facility such as Visual FoxPro®.

An example of a system implementing features of the embodiment shown in FIG. 1, as well as features of other embodiments described herein, is the MillerMed Utilities™ application available from MillerMed Software, Inc. of Bonsall, Calif. The MillerMed Utilities™ application is described further in MillerMed Utilities: The Antidote for an Organization, User Manual for Windows95 (MillerMed Software, Inc. 1998), the disclosure of which is incorporated herein by reference.

Database 18 can reside on the same computer as control module 12, administrator module 14 and tape management module 16, or database 18 can alternatively reside on a separate computer (e.g., a database server). Where database 18 is remote from the other components of office automation system 10, it may be beneficial for performance reasons to provide a local data store for temporary storage of information read from, or to be written to, database 18. Likewise, in the embodiment shown in FIG. 1, administrator module 14 and tape management module 16 access database 18 through control module 12. Alternatively, administrator module 14 and/or tape management module 16 can be given direct access to database 18.

Office automation system 10 can be implemented on virtually any type of general purpose personal computer (PC) having adequate processing power. One suitable hardware configuration includes a Pentium®-class or comparable IBM-compatible PC having at least 16 megabytes of RAM (random access memory). To take full advantage of visual and aural information that can be provided to a user of office automation system 10, the PC should have a Super VGA video card and a sound card. Similarly, to take full advantage of certain outsourcing features that can be provided in accordance with variations of the embodiment shown in FIG. 1, the PC should include a modem and/or a network interface for communicating with other computers. Finally, the PC should be coupled, either directly or indirectly, to at least one printer for report generation. In view of the different types of reports typically required in a medical office, it may be desirable to have both a laser printer or high-quality ink jet printer (e.g., for printing medical forms) and a dot matrix printer (e.g., for printing triplicate forms).

In the embodiment shown in FIG. 1, control module 12, administrator module 14, and tape management module 16 each reside on the same computer. Persons skilled in the art will recognize, however, that a wide variety of architectural arrangements are possible to meet the particular needs of any given implementation.

For example, a client-server type of arrangement may be desirable for even a small to moderately-sized medical office. In such an implementation, office automation system 10 can be installed on an applications server in communication with a plurality of client computers over a local area network (LAN). Such client computers can be used by a variety of office personnel, such as service providers (e.g., doctors, nurses) and administrative personnel, to access system functions. Similarly, database 18 can reside on a central server computer accessible by a plurality of different office automation systems 10 in remote locations. This type of arrangement is especially useful where a medical practice has a number of branch offices, thus allowing patient and administrative information to be economically shared by all of the different offices.

The embodiment illustrated in FIG. 1 is preferably implemented to maximize the use of features and capabilities provided by existing off-the-shelf software applications. For example, administrator module 14 can interface with known word processing applications, such as Microsoft Word® or Corel WordPerfect®. Database 18 can be implemented using known database applications, such as Microsoft Excel®, and can be formatted to be compatible with existing medical applications such as Medical Manager® and Physicians Office Computer®. Alternatively, a suite of such applications, such as Microsoft Office®, may be used. Other off-the-shelf applications that can be advantageously integrated with embodiments of the present invention include an event scheduler, a desktop-emulation package (e.g., PC Anywhere®, Carbon Copy®), Internet connectivity and browser software, and utility packages such as Norton Utilities®.

Figure 2:
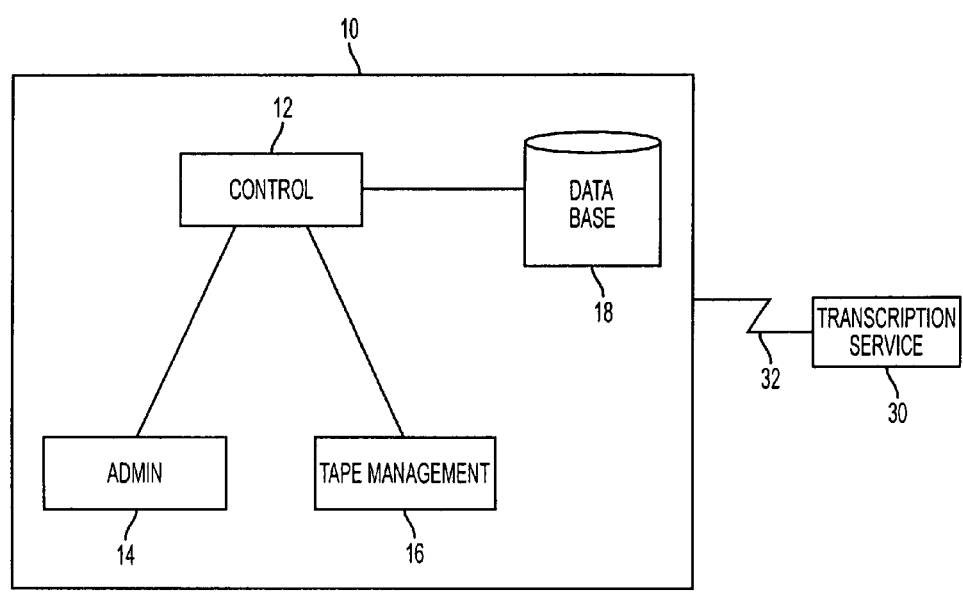
FIG. 2 is a block diagram illustrating an embodiment of the present invention wherein a system such as that shown in FIG. 1 is in communication with a remote transcription service.

In accordance with another embodiment of the present invention, illustrated in FIG. 2, office automation system 10 is electronically linked to a transcription service 30 by a communications link 32. This embodiment thus facilitates the outsourcing of tape transcription, enabling a service provider to either reallocate staff to other tasks or reduce the size of the staff (thereby reducing overhead). For this purpose, office automation system 10 includes a communications interface (not shown) for electronically exchanging data with transcription service 30. The communications interface can be implemented as customized software included in, for example, control module 12 of office automation system 10. Alternatively, or in addition, the communications interface can be implemented using an off-the-shelf communications package, including but not limited to an e-mail application. In short, any application that permits files to be exchanged between two computers is suitable. Likewise, communications link 32 can be virtually any type of communications medium, including a dial-up connection over telephone lines, a satellite connection, a wireless connection, part of a dedicated computer network (e.g., in a LAN (local area network) or WAN (wide area network)). In one particular implementation, communications link 32 comprises an Internet connection.

Office automation system 10 can also be configured to facilitate outsourcing of medical records review in much the same way as outsourcing of tape transcription. For example, rather than managing the exchange of information with transcription service 30, office automation system 10 can manage the exchange of information (e.g., medical records, reports) with an off-site record review service (not shown).

In accordance with the embodiment in FIG. 2, a given service provider would typically make a number of dictation tapes during the course of a day reflecting, for example, services provided and/or entries to be made in patient charts. Before the present invention, such tapes presented significant logistical, administrative, and staffing challenges. Various office personnel would be responsible for collecting the dictation tapes, transcribing them or assigning others to transcribe them, distributing the tapes back to the service provider for proofing, and then updating patients' charts with the transcribed reports. With this embodiment, it is now possible to outsource much of the labor associated with tape transcription, while at the same time improving the associated tracking and processing functions.

To illustrate some of the advantages of the embodiment shown in FIG. 2, consider a medical office in which one or more service providers generate a number of dication tapes in any given day. During the course of the day, the providers give tapes to a designated staff member for logging and outsourcing. Using facilities provided by tape management module 16, the staff member would input to office automation system 10 information such as the provider's name, the date the tape was made, the patient(s) to whom the tape relates. This information is used to build a table entry that will eventually be stored in database 18. In one possible implementation, the staff member would then select an off-site transcriptionist to transcribe the tape. Such selection is preferably done by choosing one of a number of possible transcriptionists presented to the staff member on a display screen. Upon selection of a transcriptionist, tape management module 16 adds to the aforementioned table entry information identifying the selected transcriptionist. Tape management module 16 can also be configured to automatically print a shipping label for each copy of each report sent to the transcriptionist. Once all identifying information is input, the table entry is stored in database 18.

At the end of the day, tapes ready for transcription are shipped to transcription service 30 using, for example, an overnight courier service. Upon completion of transcription, transcription service 30 transmits a file containing the transcribed report back to office automation system 10 over communications link 32. Tape management module 16 will update database 18 appropriately to reflect receipt of the transcription, and the transcribed report can be distributed electronically to the provider or other staff member for review. All such processing can be performed automatically in a background mode, as is known in the art, without requiring any staff interaction.

Embodiments of the present invention can be advantageously used to departmentalize the administrative functions of a medical office, significantly altering the approach typically taken to medical office administration. Many traditionally necessary interactions between office personnel can be reduced or eliminated entirely by relegating tasks to intelligent software to the maximum extent possible. For example, in accordance with another embodiment of the present invention, illustrated in FIG. 3, office automation system 10 is configured to establish a plurality of "virtual departments," each of which is directed to managing and/or performing different administrative functions. To this end, control module 12 of office automation system 10 coordinates the operations of a collection of "tracker" modules aimed at minimizing communication and document handling requirements for the office, thereby reducing personnel needs. In this particular embodiment, control module 12 is coupled to a tape tracker 40, a report tracker 42, a management tracker 44, a database tracker 46, a provider tracker 48, and an administrator tracker 50. Examples of the types of functions performed by each tracker module are presented below.

Figure 3:
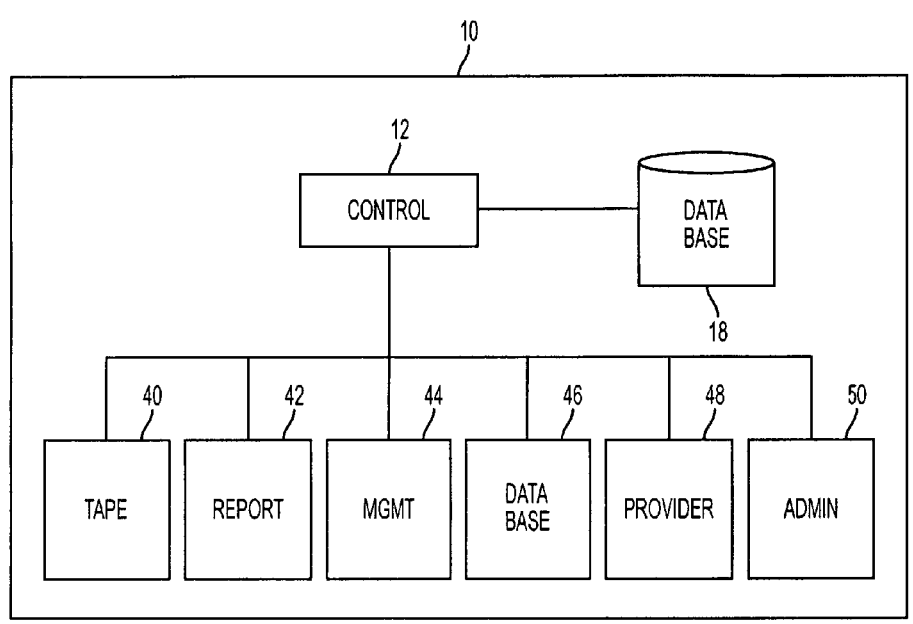
FIG. 3 is a block diagram providing a detailed view of a control module of a computer-based system for automating administrative procedures in a medical office in accordance with, for example, the embodiment shown in FIG. 1.

As is well known in the art of computer programming, the various tracker modules shown in FIG. 3 can be configured, for example, as substantially independent routines operating under the supervision of control module 12, and capable of sharing data with one another through, for example, access to database 18 or a local data store. Alternatively, the tracker modules can be configured in a master-slave relationship under close control by control module 12, operating only when expressly invoked by control module 12 and returning control to control module 12 upon completion of processing. Persons skilled in the art will recognize that a wide variety of implementations are possible, and the present invention is not limited to any particular control configuration.

Looking more closely at the individual sub-modules in the particular embodiment shown in FIG. 3, tape tracker 40 is configured to provide a comprehensive transcription management system. Tape tracker 40 provides facilities for tracking and/or reporting information relating to tapes (e.g., physical location, status), transcriptionists (e.g., name and address, number and identity of tapes assigned, current workload), record reviewers (e.g., records assigned, age of assigned records, review status), and documents (e.g., charts, invoices, shipping information), all with minimal user input.

In accordance with a particular implementation of this embodiment, tape tracker 40 includes a facility for automatically assigning tapes to transcriptionists based upon, for example, workload information maintained in database 18. For example, database 18 may include a transcriptionist table containing records for each of a plurality of transcriptionists, whether on-site or off-site. For each such transcriptionist, database 18 would include information relating to the identity and address of the transcriptionist, as well as the number of tapes currently assigned to the transcriptionist. Thus, upon being advised of a new tape to be transcribed, tape tracker 40 can identify the transcriptionist with the lightest current workload and automatically assign the new tape to that transcriptionist. Other information, such as average turnaround time, can be used to further refine the assignment of new tapes.

Report tracker 42 is configured to provide comprehensive report generation and distribution facilities, aimed at reducing the extent of user input required for these tasks. For example, report tracker 42 uses information in database 18 to automatically insert patient registration data on all reports relating to a given patient, filling in headings, captions, and carbon copy entries on all reports. In accordance with a particular implementation, report tracker 42 uses customizable templates built, for example, using standard macro features provided by most popular word processing applications (e.g., Microsoft Word®), to reduce the amount of effort required to complete reports. For instance, macros can be used to establish setup forms that enable users to easily customize report headings and establish standard text entries (i.e., boilerplate) for each provider. Similarly, customized letterhead for each branch office of a multi-branch practice can be readily provided, as well as automatically-inserted signatures for each provider.

Report tracker 42 also provides the ability to streamline report distribution. In a typical office environment, reports must be reviewed and signed by a provider, and often must also be reviewed by an editor for quality control purposes, leading to a situation in which large numbers of physical documents are constantly being passed around the office. To alleviate the logistical and administrative problems inherent in such an approach, report tracker module 42 can be configured to distribute reports electronically whenever possible. For example, providers can choose to have final versions of reports electronically copied to a personal directory accessible through office automation system 10 for review, or can select a designated editor to receive signed reports and review them, again by copying the report to the editor's personal directory. Depending upon the nature of a particular implementation, such personal directories may reside on a server computer accessible by the provider and/or editor, or on some other computer capable of communicating with the computer running office automation system 10 (e.g., an office PC capable of accessing office automation system 10 over a LAN, a home PC capable of exchanging files with office automation system 10 using e-mail).

Report tracker 42 also permits reports to be routed to designated printers on demand (e.g., by copying a file containing the report to a print directory). Indeed, persons familiar with medical office administration will appreciate that report tracker 42 allows many types of reports to be processed without ever being handled by a provider. For example, office notes, follow-ups, and other simple reports can be automatically sent by report tracker 42 directly to a printer.

Report tracker 42 can also be configured to automatically create a wide variety of standard forms, such as those associated with workers' compensation claims (e.g., notification forms, QME Summary). Such forms can be generated in batch jobs run during off-hours using information stored in database 18, and the generated reports can then be copied to appropriate directories for access when the office reopens. In certain cases, forms can be generated without any staff interaction at all based only on the registration type of each new patient. Again, such forms can be made easily customizable through the use of word processor macros.

In accordance with the embodiment shown in FIG. 3, management tracker 44 is configured to provide statistical information relating to office management for use in identifying potential problems and further streamlining operations. For example, to address the logistical problems typically associated with tracking patient charts, management tracker 44 automatically generates a daily report showing the number of charts assigned to each department in the medical office. This report can include further detailed information, setting forth the identity of each chart and its "age" (i.e., how long the chart has been in a given department). By simply consulting this report at the beginning of each day, an office administrator can ascertain a workload status for each department without ever consulting another employee.

Likewise, management tracker 44 can be configured to automatically generate and print a variety of other daily reports, including listings of past, present and future appointments; charts requiring specific action (e.g., needing a pain drawing); and identification of no-show patients with contact name and phone number. Other possible reports include database maintenance listings identifying, for example, duplicate entries and other errors; and database/file archiving information (e.g., identifying tape backups generated during overnight processing). Management tracker 44 preferably maintains a table identifying all periodic reports to be generated automatically, and such table can be readily updated by the office administrator. Programming techniques and tools for implementing this type of automatic report generation are well known in the art.

In keeping with the approach of the tracker modules already described, database tracker 46 is configured to automatically perform a variety of database maintenance activities, most or all of which preferably occur at night when the medical office is closed to avoid competition for precious computer resources. For example, records can be automatically archived after a predetermined period of inactivity (e.g., 30 days), and such archived records can be automatically removed from any and all directories to which copies had been transferred. Database tracker 46 can also be configured to automatically send e-mail notifications of required actions (e.g., report review) to appropriate personnel based upon information in the database records (e.g., age of record, status). Database tracker 46 is also responsible for constantly tracking the flow of files into and out of the office, automatically adding new clients to database 18 and automatically finding and inserting data for future patients into appropriate records. Thus, very little data entry is required after the initial input of registration information for a new patient. In addition, database tracker 46 can be configured to maintain updatable tables of information relating to employees, providers, report types, and other data for use in populating display screens with the latest available information.

Provider tracker 48 is configured to give providers access to a variety of information and facilities aimed at reducing overhead requirements and improving efficiency with respect to administrative tasks. For example, provider tracker 48 can provide a report of all currently outstanding dictations. Similarly, provider tracker 48 can give the provider access to a report of all outstanding reports, and can prioritize such reports by their respective ages. The provider thus knows how much work needs to be done, as well as what should be done first, without having to contact a staff member. In this embodiment, provider tracker 48 also provides the ability to transfer files to a diskette or to a remote computer (e.g., a home PC), and automatically distributes reports received from report tracker 42 to the appropriate provider's personal directory. Provider tracker 48 can also be configured to maintain information in database 18 relating to provider workload, thus enabling the office administrator to assess current workloads when determining to whom to assign new work (e.g., new managed care patients).

Administrator tracker 50 is configured to provide users with access to a variety of information typically required by an office administrator to perform his or her duties. For example, administrator module 52 provides instant access to management reports for each department in the medical office; reports of on-site and/or off-site data availability; instant access to provider workload, tape status, and chart location information. By maintaining all of the underlying information for such reports in database 18, administrator tracker 50 enables the office administrator to acquire an array of necessary information without the need for interactions with other office staff members. To further reduce unnecessary employee contacts, administrator tracker 50 can be configured to maintain an administrator mailbox for receiving e-mail copies of pertinent communications sent by other employees.

Figure 4:
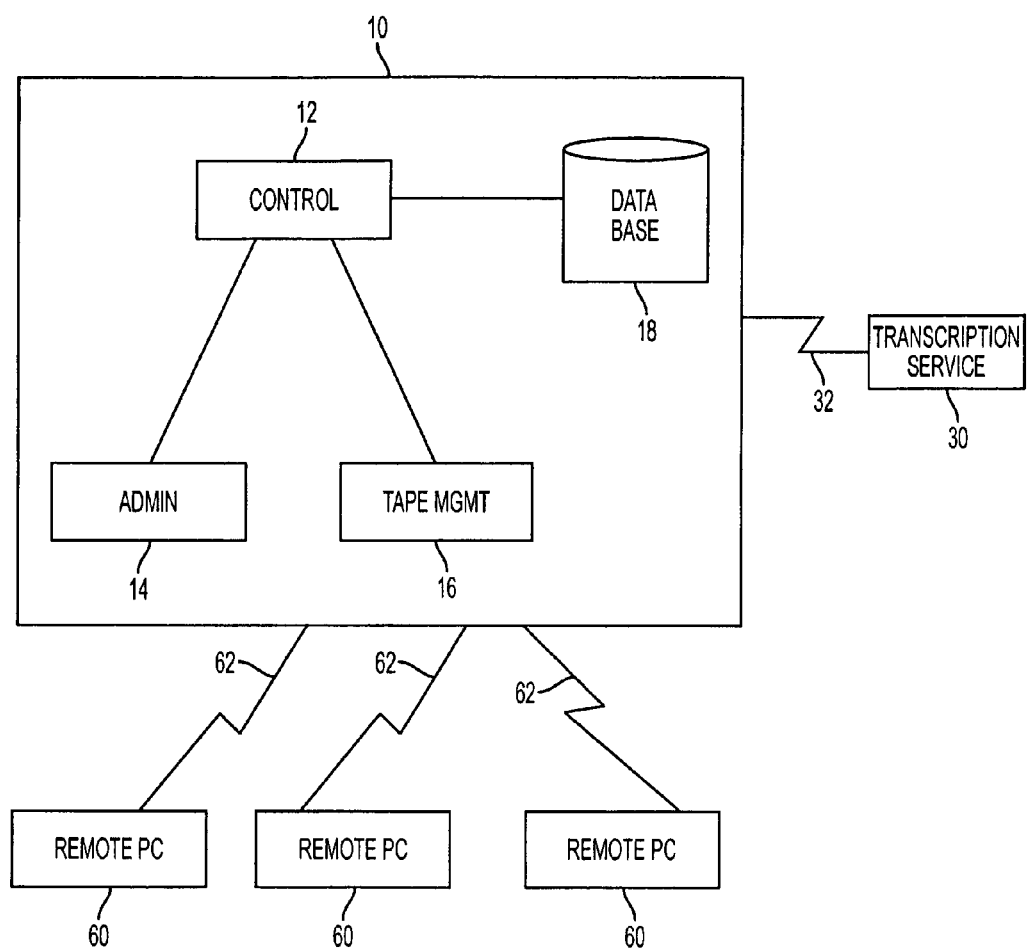
FIG. 4 is a block diagram illustrating an embodiment of the present invention wherein a system such as that shown in FIG. 1 is in communication with a remote transcription service and a plurality of remote personal computers.

Referring now to FIG. 4, in accordance with another embodiment of the present invention, office automation system 10 is accessible by remote PCs 60 over second communications links 62, thereby enabling providers or other office personnel to access system functions from locations other than the office (e.g., home). Second communications links 62 comprise, for example, dial-up connections, but the present invention is not limited to any particular communication means. Remote PCs 60 may be loaded with special software to support particular functions of office automation system 10. Alternatively, remote PCs 60 need only be capable of receiving files from and transmitting files to office automation system 10.

The embodiments described above can readily be implemented in a Microsoft Windows® environment, providing users with a familiar, user-friendly interface to the many capabilities offered by systems configured in accordance with the present invention. As is well known in the art, user interfaces can be constructed in menu form, and users can be given access to help screens, audio cues, tutorials, video demonstrations, and so on using standard facilities. Various other time-saving measures can also be built into the user interface. For example, timers can be incorporated into menus where some user selection is required. In the event no selection is made within a predetermined period of time, such as ten seconds, the program driving the menu can automatically choose the selection that would most commonly be correct in a given situation. In this way, even users with little or no system knowledge are able to benefit from the system.

In accordance with an enhancement of the foregoing embodiments, each user screen can be configured to display a bitmap image of the user associated with the logonid used to access the system. In other words, when "John Doe" logs on, his picture would appear, for example, in the upper-left hand corner of at least one open window at all times. This feature allows anyone in the area of the user to ensure that the person logged on is in fact the owner of the logonid used. Implementation of this feature is readily accomplished by storing a picture of each authorized user in respective bitmap files. When a user logs on, the logonid is used to retrieve the associated bitmap file, and the stored picture is displayed on the screen.

Figure 5:
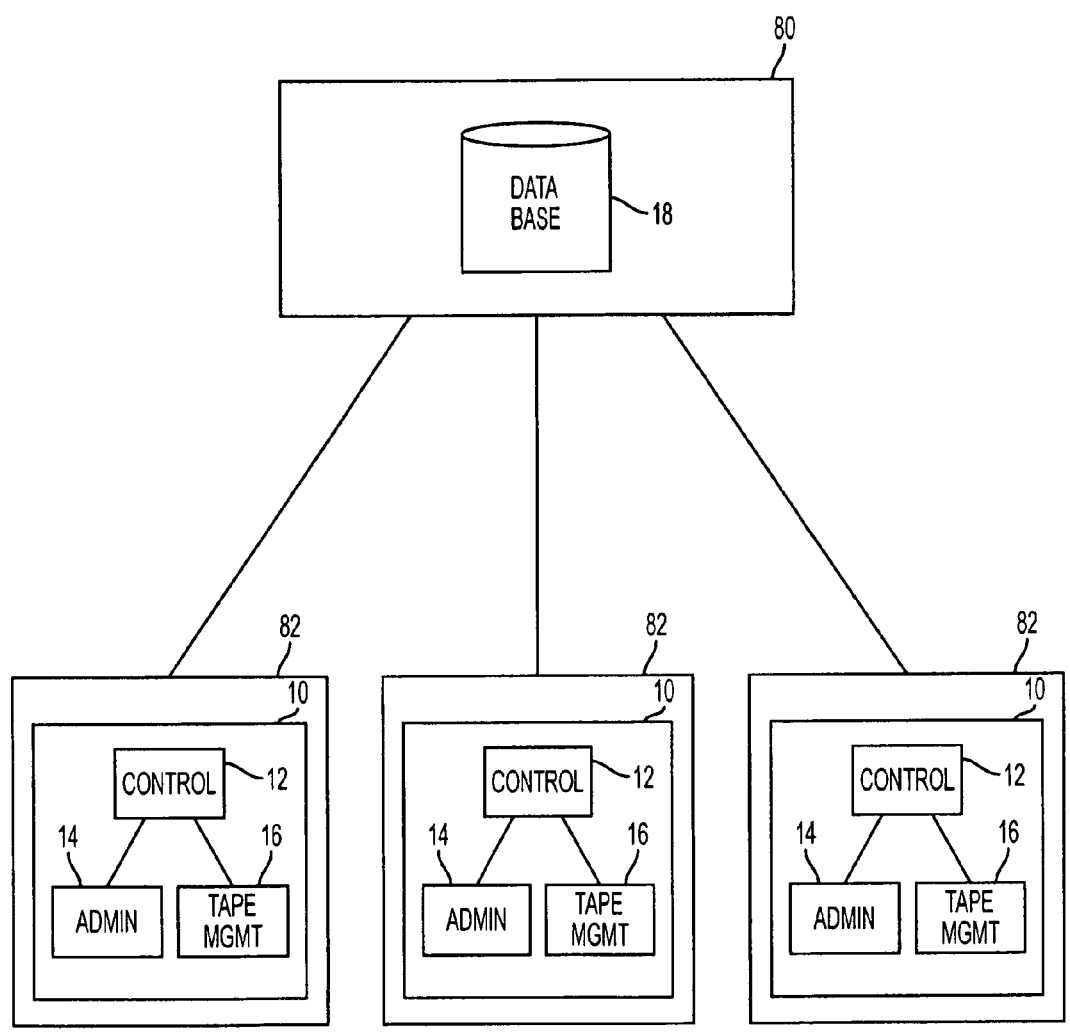
FIG. 5 is a block diagram illustrating an embodiment of the present invention wherein a plurality of client computers configured with computer-based systems for automating administrative procedures in a medical office in accordance with, for example, the embodiment shown in FIG. 1, are in communication with a server computer.

FIG. 5 illustrates an embodiment of the present invention directed to a network environment. In accordance with this embodiment, database 18 resides on a server computer 80 accessible by a plurality of client computers 82. Each client computer 82 is loaded with an instance of office automation system 10 configured, for example, as in the embodiment of FIG. 1. In contrast to the embodiment in FIG. 1, however, database 18 does not reside on the same computer as office automation system 10. Such an arrangement is especially useful where, for example, a practice has a number of different branches at which the same patients may be seen, since the shared use of database 18 eliminates the need to maintain duplicate data at each of the multiple locations. For performance reasons, a copy of selected records from database 18 can be cached in local memories (not shown) of client computers 82. Updates in progress can be made to the cached record and then copied to database 18 upon completion. As is known in the art, particularly with respect to Internet applications, client computer 82 can be configured to determine whether such a locally cached record has been updated on database 18 and, if so, to automatically replace the cached version with a copy of the updated version.

Figure 6:
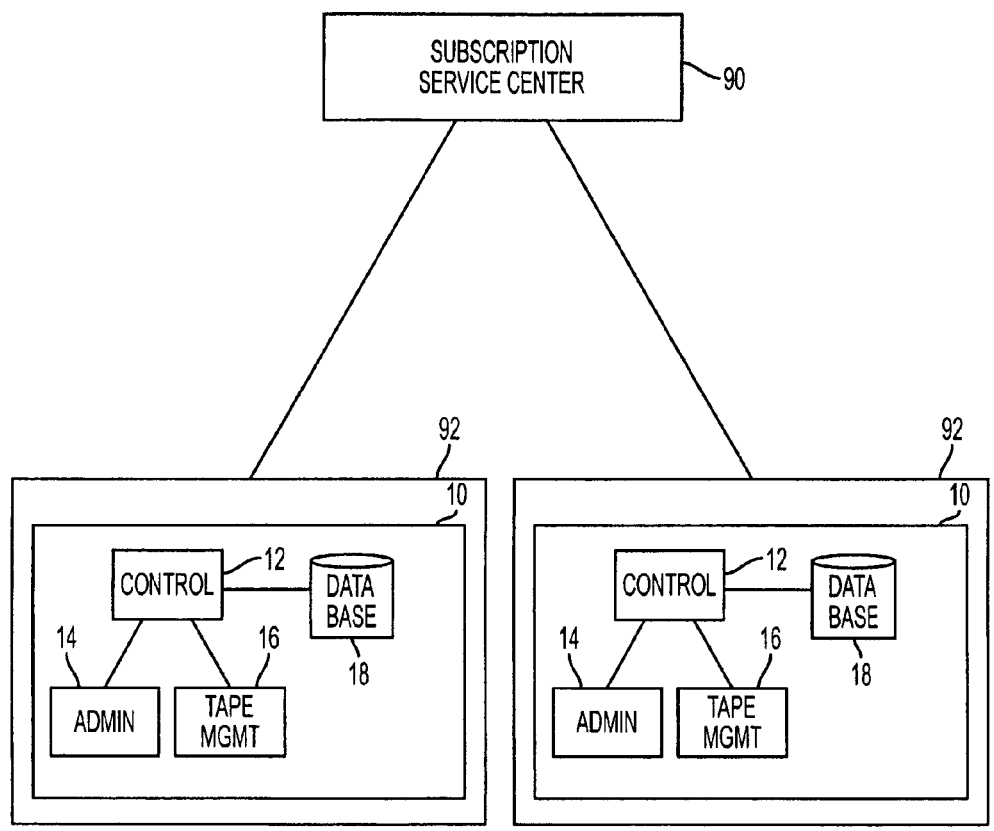
FIG. 6 is a block diagram illustrating an embodiment of the present invention wherein a plurality of computers configured with computer-based systems for automating administrative procedures in a medical office in accordance with, for example, the embodiment shown in FIG. 1, are in communication with a subscription service center.

Referring now to FIG. 6, in accordance with another embodiment of the present invention, an office automation system 10 such as that shown in FIG. 1, is provided as part of a subscription service, thereby offering a variety of off-site services to providers in remote locations. In accordance with such an arrangement, services can be paid for as they are used. Thus, a solo practitioner with only periodic need for transcription services has comparable access to the features and benefits of office automation system 10 and associated subscription services as does a large medical group that may choose to use the system for overflow dictation or to outsource large volumes of clerical work.

As shown in FIG. 6, each of a plurality of subscriber computers 92 are in communication with a subscription service center 90. In one particular implementation of this embodiment, subscription service center 90 comprises an office location and a server computer (not shown) accessible over the Internet. Each subscriber computer 92 has loaded thereon office automation system 10 configured, for example, like the embodiment of FIG. 1. It should be appreciated, however, that each subscriber computer 92 could actually comprise a server maintained by a particular practice group, to which are connected a number of individual computers used by providers, administrators, and other personnel.

In accordance with the embodiment shown in FIG. 6, a number of different types of services can be offered on a subscription basis, including but not limited to tape transcription, record review, and chart preparation. In addition, all of the necessary tracking and reporting associated with these services can also be provided.

With respect to transcription, the level of service provided is fully customizable to the needs of any particular subscriber. For example, a provider can simply dictate a tape during an office hours session and send it to subscriber service center 90 (e.g., by overnight delivery service). Subscriber service center 90 would then arrange for transcription (either on-site or using an off-site vendor), print the report and make all copies, mail and/or e-mail the reports and copies back to the subscriber, and update the subscriber's database 18 to document progress. In a particular implementation, subscriber service center 90 periodically updates database 18 with the progress of the requested service, thereby enabling the subscriber to use office automation system 10 to access status information. Once the file containing the transcription is transmitted or otherwise loaded into database 18, the subscriber can view, print, or edit the transcription using the above-described facilities of office automation system 10.

Many variations of the foregoing transcription service are possible. For example, where a subscriber has its own transcriptionist, transcription files can be sent by diskette or electronically to subscriber service center 90, after which subscriber service center 90 can print and mail reports and update the subscriber's database 18 as just described. If a subscriber wishes to transcribe and print tapes on-site, subscriber service center 90 can receive the transcription files, process them, and transmit files containing the desired reports to office automation system 10 for automatic printing on the subscriber's printer. Similarly, if a subscriber wishes to use a particular off-site transcriptionist, subscriber service center 90 can receive transcription files from the transcriptionist either electronically or on diskette. As before, such files can then be processed and reports either printed and shipped by subscriber service center 90, or transmitted to the subscriber computer 92 for printing. In either case, chart copies are shipped to the subscriber.

Subscriber service center 90 can also provide record review services, performing quality control checks on transcribed dictations and/or on records and reports generated from transcription files. Likewise, subscriber service center 90 can prepare charts. For example, a complete set of history forms, status forms, and fee tickets for an entire office session of patients, complete with patient information imprinted, can be delivered directly to any subscriber office location.

Subscriber service center 90 can also provide special services to subscribers on demand, such as binding, preparation of slides, and preparation of other presentation materials for lectures, academic conferences, and so on. Facilities built into office automation system 10 for exchanging files with subscriber service center 90 can readily be used for forwarding the underlying information to subscriber service center 90 along with appropriate instructions. By providing for Internet access and/or direct modem connections, subscriber service center 90 can offer maximum flexibility to providers who are traveling. Any subscriber can then access subscriber service center 90 from a remote location to gain access to their particular practice's data, retrieve reports, or drop off work. Subscriber service center 90 can also provide data archiving services, freeing up resources on the subscriber's system that might otherwise have to be dedicated to storing outdated records. Access to archived records can then be provided on-demand by subscriber service center 90.

It should be emphasized that the foregoing subscription services are described by way of example only. Persons in the medical field will recognize that many other services, both administrative and otherwise, can be provided on a subscription basis using arrangements such as that shown in FIG. 6.

Office automation systems configured in accordance with embodiments of the present invention can be distributed, for example, as a set of instructions residing on a storage medium. Such a storage medium might be a portable storage device, such as a diskette or a CD-ROM; a memory of a computer; a piece of firmware; or any other medium on which it is known to store executable instructions.

The foregoing is a detailed description of particular embodiments of the present invention. The invention embraces all alternatives, modifications and variations that fall within the letter and spirit of the claims, as well as all equivalents of the claimed subject matter. Persons skilled in the art will recognize from the foregoing description that many other alternatives, modifications and variations are also possible.

What is claimed is:

1. A computer implemented system for automating administrative procedures in a medical office, comprising:
   A. a database;
   B. a tape tracker module;
   C. a report tracker module;
   D. a management tracker module;
   E. a database tracker module;
   F. a provider tracker module;
   G. an administrative tracker module; and
   H. a control module;
   I. wherein the tracker modules are configured to operate under control of the control module and to share data with one another via access to the database;
   J. wherein the tape tracker module is configured to:
      (1) track physical location of transcription tapes;
      (2) track current status of the transcription tapes;
      (3) identify transcriptionists responsible for transcribing the tapes;
      (4) identify tapes assigned to a particular transcriptionist;
      (5) track current transcription workload assigned to a particular transcriptionist;
      (6) automatically assign a particular tape to a particular transcriptionist based on a predefined criteria including the current transcription workload assigned to the particular transcriptionist;
      (7) automatically, upon electronic receipt of a transcribed report, distribute the report to a provider or staff member for review;
      (8) identify record reviewers responsible for reviewing medical records;
      (9) track age of the records assigned to a particular record reviewer;
      (10) track current review status of the records; and
      (11) identify documents related to office administration;
   K. wherein the report tracker module is configured to:
      (1) automatically insert into appropriate reports patient information including registration data;
      (2) enable a health care provider to choose to have final versions of reports to be electronically copied to the provider's personal directory for review;
      (3) enable a health care provider to select a designated editor to receive signed reports and review them by electronically copying the reports to the editor's personal directory;
      (4) automatically route certain types of reports to a printer; and
      (5) automatically generate standard forms based on patient information from the database in batch jobs during off-hours;
   L. wherein the management tracker module is configured to:
      (1) provide statistical administrative information relating to office management;
      (2) automatically generate a report showing the number of charts assigned to each department in the medical office;
      (3) automatically generate a report showing an age of charts assigned to each department so that an office administrator may ascertain a workload status for each department;
      (4) automatically generate a report showing listings of past, present and/or future appointments;
      (5) automatically generate a chart that requires specific action to be taken; and
      (6) automatically generate a report identifying no-show patients;
   M. wherein the database tracker module is configured to:
      (1) automatically archive records;
      (2) automatically e-mail notifications of required action to appropriate medical personnel;
      (3) track flow of files into and out of the office;
      (4) automatically add new patients to the database; and
      (5) automatically find and insert data for future patients into appropriate database records;
   N. wherein the provider tracker module is configured to:
      (1) provide a report of all outstanding dictations;
      (2) provide a report of all outstanding reports; and
      (3) maintain information in the database relating to provider workload to enable an office administrator to assess current workloads when determining to whom to assign new patients;
   O. wherein the administrative tracker module is configured to:
      (1) provide access to management reports for each department;
      (2) provide access to reports of on-site and/or off-site data availability; and
      (3) provide access to provider workload, tape status, and chart location information.

2. The system of claim 1, wherein the age of a particular record tracked by the tape tracker module represents the amount of time that has lapsed since the particular record was assigned for review.

3. The system of claim 1, wherein the documents related to office administration tracked by the tape tracker module include charts, invoices and shipping information.

4. The system of claim 1, wherein the criteria on which a particular tape may be assigned by the tape tracker module includes average turnaround time.

5. The system of claim 1, wherein the tape tracker module is configured to present one of a number of possible transcriptionists to a staff member on a display screen for selection.

6. The system of claim 5, wherein upon selection of one of the number of possible transcriptionists, the tape tracker module is configured to automatically print a shipping label for copy of each tape to be sent to the transcriptionist.

7. The system of claim 1, wherein the tape tracker module is configured to manage an exchange of medical records and/or reports with an off-site record review service.

8. The system of claim 1, wherein the automatic inserting of patient information into reports by the report tracker module includes use of macro features provided by existing word processing applications.

9. The system of claim 8, wherein the use of macro features provides customized letterhead for each branch office of a multi-branch practice.

10. The system of claim 8, wherein the use of macro features provides automatically-inserted signatures for each health care provider.

11. The system of claim 1, wherein the report tracker module is configured to provide the final versions of reports for review to the provider via copying the report to the provider's personal directory.

12. The system of claim 1, wherein the report tracker module is configured to provide the final versions of reports for review to the designated editor via copying the report to the designated editor's personal directory.

13. The system of claim 1, wherein the certain types of reports automatically routed to a printer by the report tracker module include office notes and follow-ups.

14. The system of claim 1, wherein the standard forms automatically generated by the report tracker module include those associated with worker's compensation claims.

15. The system of claim 1, wherein the report tracker module is configured to copy the generated standard forms to appropriate directories for access when the medical office reopens.

16. The system of claim 1, wherein at least one of the reports generated by the management tracker module is generated daily and automatically printed.

17. The system of claim 1, wherein a report generated by the management tracker module includes age of a chart representing how long the chart has been in a given department.

18. The system of claim 1, wherein the specific action to be taken in the chart generated by the management tracker module includes attachment of a pain drawing.

19. The system of claim 1, wherein reports generated by the management tracker module include database maintenance listings identifying duplicate entries and database/file archiving information.

20. The system of claim 19, wherein the database/file archiving information includes tape backups generated during overnight processing.

21. The system of claim 1, wherein the database tracker module is configured to remove the archived records from any directory to which copies had been transferred.

22. The system of claim 1, wherein the database tracker module is configured to e-mail notification of a report review based on record status information stored in the database.

23. The system of claim 1, wherein the provider tracker module is configured to automatically distribute reports received from the report tracker module to the appropriate provider's directory.

24. The system of claim 1, wherein the administrative tracker module is configured to maintain an administrator mailbox for receiving e-mails of pertinent communications sent by other employees.

* * * * *